(12) United States Patent
Dunn et al.

(10) Patent No.: US 8,775,200 B1
(45) Date of Patent: Jul. 8, 2014

(54) SYSTEM AND METHOD FOR GENERATING PATIENT HEALTH MANAGEMENT INFORMATION

(75) Inventors: Daniel L. Dunn, Bedford, MA (US); Michael Manocchia, Cumberland, RI (US)

(73) Assignee: OptumInsight, Inc., Eden Prairie, MN (US)

( * ) Notice: Subject to any disclaimer, the term of this patent is extended or adjusted under 35 U.S.C. 154(b) by 810 days.

(21) Appl. No.: 12/195,858

(22) Filed: Aug. 21, 2008

(51) Int. Cl.
*G06Q 50/00* (2012.01)
*G06Q 40/00* (2012.01)
*G06F 7/00* (2006.01)

(52) U.S. Cl.
USPC .................................. 705/2; 705/4; 707/690

(58) Field of Classification Search
USPC ......................................................... 705/2, 3
See application file for complete search history.

(56) References Cited

U.S. PATENT DOCUMENTS

| | | | | |
|---|---|---|---|---|
| 5,365,425 | A | * | 11/1994 | Torma et al. ....................... 705/2 |
| 5,706,441 | A | * | 1/1998 | Lockwood ......................... 705/3 |
| 5,835,897 | A | * | 11/1998 | Dang ................................. 705/2 |
| 2004/0254816 | A1 | * | 12/2004 | Myers ............................... 705/2 |
| 2005/0182659 | A1 | * | 8/2005 | Huttin .............................. 705/2 |
| 2008/0124689 | A1 | * | 5/2008 | Williams et al. .............. 434/236 |
| 2009/0150188 | A1 | * | 6/2009 | Castille ........................... 705/3 |

OTHER PUBLICATIONS

Anonymous, "Ingenix Announces New Clinical Care Groups' Episode Grouping Tool with Integrated Pharmaceutical Data," Apr. 12, 2000, PRNewswire, (2 pages).*

* cited by examiner

*Primary Examiner* — Rachel L Porter
(74) *Attorney, Agent, or Firm* — Bridget M. Hayden; Dorsey & Whitney LLP

(57) ABSTRACT

A computer-implemented system and method utilizes patient claim data, including medical, pharmaceutical, laboratory claims, and self-report survey data to classify patients into one or more health management groups (HMGs) relating to one or more particular diseases, health conditions or health pre-conditions, each having an associated severity level that indicates the severity of the patient's condition. The HMGs assigned to each patient (e.g., health plan member) enable users of the system and method to identify patients having particular diseases, health conditions and pre-conditions based not only upon the patients' claim data but also based upon the patients' self-report survey data obtained from various sources. The HMGs assigned for each patient also enable the user to identify the severity of the patient's disease, condition or pre-condition to facilitate intervention and/or preventative care of the patient.

11 Claims, 9 Drawing Sheets

| Member HMG | Total Rows: 99 | 1 of 1 | 200 ▽ | | | | | | | | |
|---|---|---|---|---|---|---|---|---|---|---|---|
| Columns | Filter | Save | | Current report shows all members. Get started by reviewing members in the report below, or by filtering by key criteria to refine your search. | | | | | | | |
| | Links to HMGs | | | | | | | | | | |
| Member ID | Intvntn. Opps. | Smoking Tobacco | Obesity | Exercise | Sex | Age | Months Enrolled | Future Risk, Costs | Primary Risk | Summary Behavior Score | Summary Attitude Score | Social Score |
| 00000000001 | ■ | □ | ■ | ▨ | Female | 71 | 12 | 29.71 | Diabetes | | | |
| 00000000002 | ■ | ▨ | ■ | ■ | Female | 48 | 12 | 24.14 | Hypertension | | | |
| 00000000003 | □ | □ | □ | □ | Female | 57 | 12 | 17.75 | COPD/Asthma | | | |
| 00000000004 | ■ | □ | ▩ | ▨ | Male | 55 | 12 | 16.42 | Diabetes | | | |
| 00000000005 | ▩ | □ | ■ | ▨ | Male | 35 | 12 | 13.19 | Other neuro. | | | |
| 00000000006 | ■ | ■ | □ | □ | Female | 61 | 12 | 9.15 | CHF | | | |
| 00000000007 | ▩ | | ▩ | ▨ | Female | 56 | 12 | 9.09 | Other mental | | | |
| 00000000008 | ■ | □ | □ | □ | Female | 51 | 12 | 8.99 | CAD | | | |

SYSTEM AND METHOD FOR GENERATING PATIENT HEALTH MANAGEMENT INFORMATION

FIELD OF THE INVENTION

The present invention generally relates to a computer-implemented system and method in which patient claim data, including medical, pharmaceutical, biometric and laboratory claims, and self-report survey (SRS) data are utilized to classify patients into one or more health management groups (HMGs) relating to one or more diseases, health conditions or health pre-conditions, wherein each HMG has an associated severity level that indicates the severity of the patient's condition and facilitates intervention and preventative care.

BACKGROUND OF THE INVENTION

Existing systems currently support the analysis of medical and pharmaceutical claim data by various units of analysis, including populations or members, episodes of care of diseases/conditions/syndromes, and utilization, including cost and risk variables. These known systems typically use patients' health-related claim data (e.g., historical medical and/or pharmacy insurance claims) to group each patient's claim data into units of analysis, which are subsequently utilized to generate an assessment of a patient's health. For example, a known method for grouping medical and/or pharmacy claims is described in U.S. Pat. No. 5,835,897, entitled Computer-Implemented Method for Profiling Medical Claims.

However, patient health may be influenced by variables that are not reflected or accounted for in the patient's medical and/or pharmaceutical claim data. Factors influencing a patient's health may include demographic variables, patient behavior, the patient's overall quality of life. One model for health-related quality of life was published in 1995 in the article "Linking Clinical Variables with Health-Related Quality of Life: A Conceptual Model of Patient Outcomes," by I. B. Wilson and P. D. Cleary in the Journal of the American Medical Association (JAMA). The Wilson-Cleary model identifies the characteristics of the individual, the characteristics of the environment, biological function, symptoms, functional status, general health perceptions, and overall quality of life as variables influencing the full picture of a patient's health.

Currently, there is a need for a computer-implemented system that enables analysis and assessment of patients' health and facilitates patient intervention and preventive care by taking into account a patients' biology, symptoms, functional health, health attitudes and behaviors, and well-being.

SUMMARY OF THE INVENTION

In view of the limitations of existing systems described above, the present invention provides a computer-implemented system and method for generating health management data for one or more patients relating to a particular disease, health condition, or health pre-condition (indicating a heightened likelihood or tendency that a person will have a disease or health condition in the future). The health management data generated by the system and method comprises health management groups that are assigned to one or more patients, each having an associated severity level, that enable users of the system and method to identify patients having particular diseases, health conditions and pre-conditions based not only upon their claim data but also based upon self-report survey (SRS) data obtained from various sources. The health management data further enables users to identify the severity of the disease, condition or pre-condition, of each patient to facilitate intervention and/or preventative care of the patient.

The use of SRS data to classify patients into HMGs enables the system and method of the present invention to identify patient conditions and pre-conditions having no defined medical, laboratory or pharmaceutical codes, or for which little or no claim data exists, and also enables identification of health-related issues that do not fall within traditional medical categories, such as poor nutrition, inadequate exercise, tobacco use, stress, etc., and pre-conditions such as a heightened likelihood of developing diabetes, asthma, obesity, etc., which may not be identifiable using claim data.

A computer-implemented method for generating health management data for one or more patients relating to a particular disease, health condition or pre-condition in accordance with the present invention, may include: storing a plurality of health management groups, each relating to a disease, health condition or pre-condition and including one or more medical codes associated with the disease, health condition, or pre-condition, wherein each health management group has an associated severity level; storing mapping data that enables mapping of SRS data to one or more of the stored health management groups; receiving medical claim data and SRS data associated with a patient; determining whether the medical claim data for the patient contains one or more of the stored medical codes associated with the disease, health condition or pre-condition; assigning the patient to a first health management group having a first associated severity level based upon the presence or absence of medical codes in the patient's medical claim data; assigning the patient to a second health management group having a second severity level using the patient's SRS data and the stored mapping data; reconciling the first and second health management groups using predefined reconciliation rules to generate a final health management group assignment for the patient for the disease, health condition or pre-condition; and storing the final health management group generated for the patient. This method additionally may include generating display data that graphically displays the final health management group for the patient.

The computer-implemented system and method according to the present invention also may be implemented to enable identification of medical and health-related problems and conditions for which there are no standardized diagnosis, treatment, procedure, or drug codes. In such cases, the system and method utilize SRS data to generate health management data for one or more patients. In such an implementation, a computer-implemented method for generating health management data for one or more patients relating to a particular disease, health condition or pre-condition, may include: storing a plurality of health management groups, each associated with a disease, health condition or pre-condition, wherein each health management group has an associated severity level; storing mapping data that enables mapping of patient SRS data to one or more of the stored health management groups; receiving SRS data associated with a patient; assigning the patient to a health management group having an associated severity level using the patient's SRS data and the stored mapping data; and storing the health management group assigned to the patient.

The above-described methods may be performed by computer systems such as those described in the present application.

These and other features and advantages of the present invention will become apparent to those skilled in the art from the following detailed description, wherein it is shown and described illustrative embodiments of the invention, including best modes contemplated for carrying out the invention. As it will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 5-9 provide exemplary graphic displays of health management data generated in accordance with the present invention.

DETAILED DESCRIPTION

Figure 1:
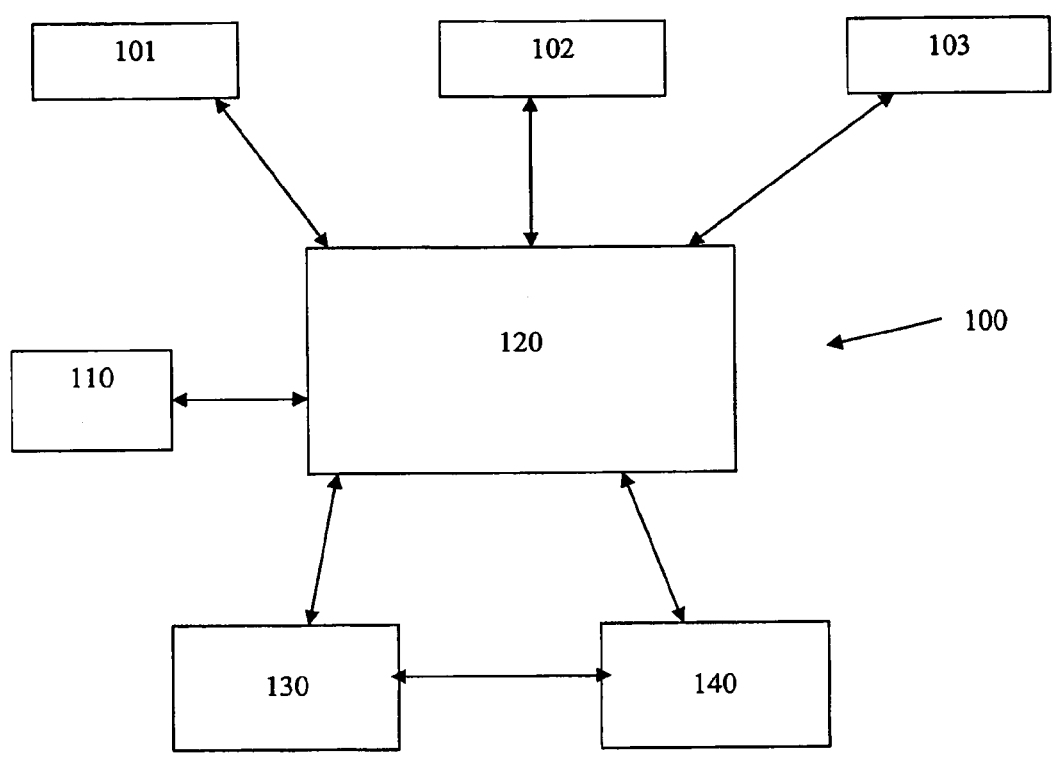
FIG. 1 depicts a system for generating health management information for one or more patients in accordance with the present invention.

With reference to FIG. 1, a system 100 for generating health management information (data) for one or more patients, such as members of a health plan, relating to one or more diseases, health conditions and/or pre-conditions, includes one or more data sources, such as data sources 101, 102, and 103; data storage 110 for storing health management groups (HMGs) including definitions and related information for one or more diseases, health conditions and/or pre-conditions, and mapping data to enable mapping of patient SRS data to one or more of the HMGs; an HMG processor 120; data storage 130 (such as a data warehouse) for storing the health management data generated by the HMG processor 120 along with claim data and self-report SRS data for each patient, and an optional system 140 that accesses the output files from the HMG processor 120 stored in storage 130 to generate user displays or enable users to access the HMG output files and patient data, as discussed below in greater detail.

The inputs 101, 102, and 103 shown in FIG. 1 each represent any of a variety of data inputs that may be provided to feed the HMG processor 120. Inputs 101, 102, and 103 may provide one or more types of data associated with one or more patients, including medical claim data, pharmaceutical claim data, laboratory claim data, severity of illness data, and SRS data, such as laboratory values, biometric data, demographic data, consumer-based data, contextual variables, health behavior information, and any other types of data that may assist in providing a comprehensive assessment of each patient's health and health management. In some implementations, SRS data may be obtained from patients in the form of answers to survey questions, such as surveys taken via web browser or other automated or manual means. SRS data, such as data obtained through patient or caregiver surveys, may be formatted into a predefined format to enable processing by HMG processor 120 as described in detail below.

Medical, laboratory and/or pharmacy claim data for each patient may include all historical claim data available for the patient over a predefined period of time. For example, claim data input into the HMG processor 120 may include all claim data available for a patient for the previous year, two years, five years, etc. Alternatively, all available claim data for each patient, regardless of date, may be provided as an input to HMG processor 120. A patient's claim data may include claims representing medical or health-related services, procedures or treatments rendered to the patient, pharmacy claims, laboratory claims, and/or any other type of health-related claims associated with each patient.

Prior to being provided to HMG processor 120, the available claim data for each patient or member to be analyzed may be processed to validate the data (e.g., to ensure that the claims include the data fields required by the HMG processor). In some implementations, the claim data may also be categorized or grouped based upon the type of disease, condition, service or drug described in each claim record. One exemplary method for validating medical and pharmaceutical claim records is described in U.S. Pat. No. 5,835,897, entitled, "Computer-Implemented Method for Profiling Medical claims," which is incorporated by reference herein. In one implementation of the present invention, some or all of the fields in the ETG output file created for each patient by the grouping method described in the '897 patent are provided as inputs to HMG processor 120.

Health risk and/or severity of illness information may also be provided as an input to HMG processor 120. Health risk information may include, for example, risk scores that are calculated using predictive models, such as predicted patient healthcare cost and utilization rates generated by ImpactPro® available from Ingenix, Inc. of Eden Prairie, Minn.

Disease and illness information that may be provided as an input to HMG processor 120 may be generated, for example, using a methodology described in U.S. Pat. No. 5,835,897, which is incorporated by reference herein. In the methodology described in the '897 patent, episode treatment groups (ETGs) are assigned to patients' medical and/or pharmacy claim data based upon the contents of the claims (e.g., the type of service, procedure, or prescription drug provided to the patient). Thus, the ETGs assigned to a patient's claim data as described in the '897 patent may represent a particular mix of diseases or health-related conditions for the patient and their severity(ies). The ETGs associated with the patient may be provided as an input to the HMG processor 120.

A comparison of a patient's medical care with clinical guidelines and protocols may be provided as an input to HMG processor 120, for example, using a methodology described by the Ingenix Evidence-based Medicine (EBM) Connect application. EBM Connect assesses a patient's care against clinical guidelines and protocols and identifies opportunities for care improvement and intervention. The opportunities provide information to facilitate intervention and the provision of preventive care. The EBM Connect assessments associated with the patient may be provided as an input to the HMG processor 120.

Laboratory values obtained from laboratory tests associated with a patient may also be provided as an input to HMG processor 120. Additionally, biometric data associated with each patient, such as body mass index, weight, blood pressure, etc., may also be provided as an input into HMG processor 120. Such information may be directly measured, obtained from laboratory data, and/or collected as self-report survey (SRS) data, for example, in response to patient survey questions. Biometric data may also be collected using any other devices or methods, including automated or manual electronic monitoring or measuring devices or methods, or obtained via survey responses.

Demographic data associated with each patient may be gathered from the patient's claim data and/or from survey responses and provided as an input to HMG processor 120. Demographic data may include, for example, age, gender, geographical location data associated with each patient.

Consumer-based data may include data associated with the purchasing and spending habits and/or financial status of patients. In one implementation, patients' consumer-based data may be obtained from credit institutions, such as banks or credit card issuers.

Contextual variables (e.g., where a patient lives or family composition) and/or health-related behavior information (e.g., smoking, nutrition, physical activity) may also be provided as inputs to HMG processor 120. This information may be provided in the form of SRS data that has been formatted into a predefined format to enable processing by HMG processor 120 as described in detail below.

Data storage 110 is provided to store health management group (HMG) definitions and related information for one or more diseases, health conditions and/or pre-conditions, and mapping data to enable mapping of a patient's SRS data and any other types of patient information as discussed above to one or more of the HMGs. Each HMG is a defined unit of analysis that may be used, for example, to identify, stratify, and/or segment a population of patients (such as members of a health plan) based upon a selected disease, medical or health-related condition, or pre-condition and the severity of the patient's disease, condition or pre-condition. This identification, stratification or segmenting of patients using HMGs further may be utilized to identify patients who qualify for various types of intervention, preventative treatment, or treatment.

Exemplary generic HMGs that may be defined and stored in storage 110 are defined as follows:

Disease A:
HMG 1—Disease A, Severity 0 (Does Not Have Disease)
HMG 2—Disease A, Severity 1 (Low Severity)
HMG 3—Disease A, Severity 2 (Moderate Severity)
HMG 4—Disease A, Severity 3 (High Severity) Health Condition B:
HMG 5—Health Condition B, Severity 0 (Does Not Have Condition)
HMG 6—Health Condition B, Severity 1 (Low Severity)
HMG 7—Health Condition B, Severity 2 (Moderate Severity)
HMG 8—Health Condition B, Severity 3 (High Severity) Pre-Condition C:
HMG 9—Pre-Condition C, Severity 0 (Does Not Have Pre-condition)
HMG 10—Pre-Condition C, Severity 1 (Low Severity)
HMG 11—Pre-Condition C, Severity 2 (Moderate Severity)
HMG 12—Pre-Condition C, Severity 3 (High Severity)

Each HMG listed above further may comprise (1) a definition based on one or more types of diseases, diagnoses, procedures, treatments, drugs, laboratory data, etc., as would be identifiable from the patient's claim data (including medical, pharmacy and laboratory claims) and/or (2) a definition based on SRS data, for example, collected from each patient or healthcare provider via computer-implemented questionnaires or surveys.

HMG assignments based on claims, patient demographic, lab results and biometric data (claim-based HMGs) may be defined to include age and gender and specific ICD-9, DCC, NDC, CPT, HCPC and other types of medical, drug, and laboratory result codes. Additionally, if the claim data is pre-grouped into diagnostic groups, such as episode treatment groups (ETGs) discussed above, or the claims data is used to identify the compliance of the patient with clinical guidelines or protocols, such as using EBM Connect, as described above, the claim-based HMG may also be defined to include one or more ETGs or other diagnostic groups or patient compliance findings that may be assigned using the patient claim data.

SRS-based HMGs are defined based upon certain types or values of SRS data. For example, if a patient has certain types or values of SRS data, the patient's SRS data may satisfy the definition of one or more HMGs, such that the patient will be mapped to the HMG. In one implementation of the present invention, all claim data is pre-processed prior to being input into the system 100 to ensure that the claim data is complete, valid and provided in a defined format.

In one implementation, SRS data received from data inputs, e.g., 101, 102, and/or 103 in FIG. 1, is formatted in accordance with predefined formatting definitions. The formatted SRS data is then mapped into a processable format or data groups that can be utilized by the HMG processor 120 to determine whether the patient is grouped into one or more HMGs. The formatted SRS data may be mapped into the processable format or data groups and then assigned to an HMG by HMG processor 120 using mapping data or definitions stored in storage 110. Examples of mapping data and formatted SRS data are provided below.

Patient data requirements may differ for each HMG. For example, some HMGs require that claim data be available for the patient for a defined period of time, such as at least one year. Some HMGs require that SRS data be available for the patient for a defined period of time, such as at least one year. Some HMGs may require that both claim and SRS data be available for a defined period of time. For some HMGs, laboratory data from either claims or SRSs must be available within a certain time period (for example, within the past year).

Thus, the inputs that are necessary for the HMG process performed by processor 120 may vary based upon the definition and requirements of each potentially applicable HMG. As illustrated in the examples of HMGs provided below relating to sleep problems and alcohol-related problems, each HMG is defined to require certain data inputs for each patient in order to determine whether the patient falls within the HMG, and, if so, the appropriate level of severity of the HMG. The HMGs stored in storage component 110 may be defined to require any one or more of the various types of inputs described above with reference to inputs 101, 102 and 103 in FIG. 1. The required inputs for each HMG are prerequisites that must be provided to enable HMG processor 120 to assign each patient to an HMG.

System 100 may be implemented using known computer technology, such as a combination of data processors, storage devices, data servers, data formatting devices, and data communication devices as are known in the art. Additionally, the components of system 100 illustrated in FIG. 1 may be configured, combined or divided into additional components as desired by the implementer of the system. For example, one storage device may be provided to serve the storage functions of components 110 and 130, or processor 120 may also perform the display generation functionality of component 140.

Figure 2:
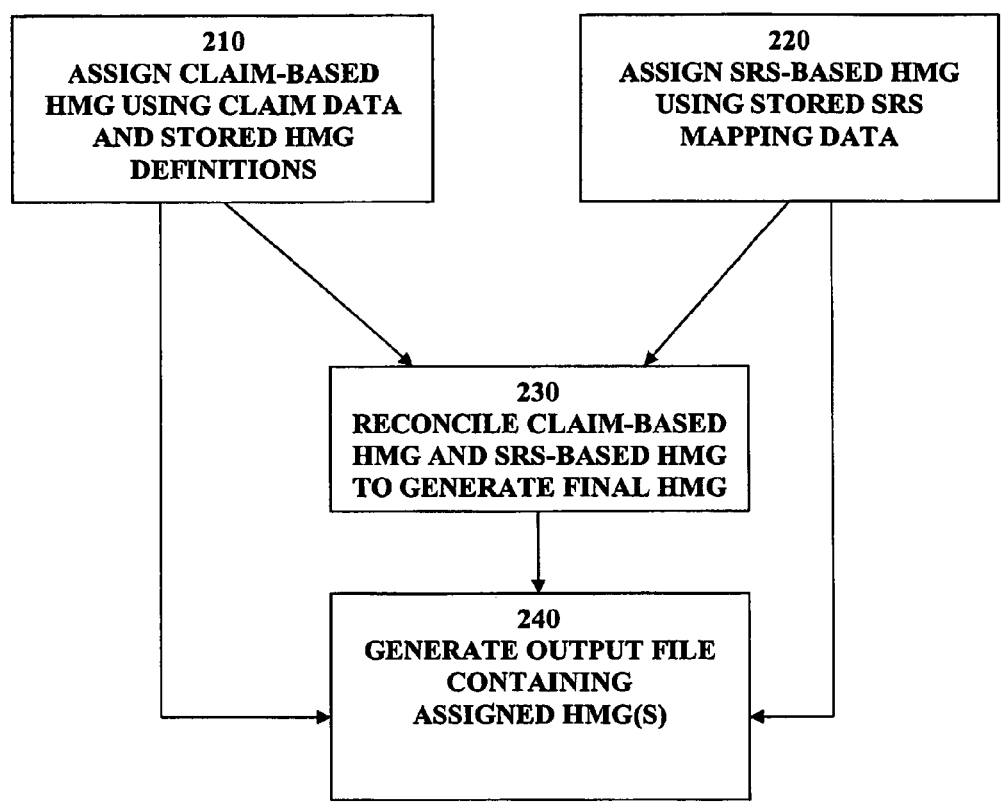
FIG. 2 provides a flow chart of a method for assigning health management groups for one or more patients in accordance with the present invention.
Figure 3:
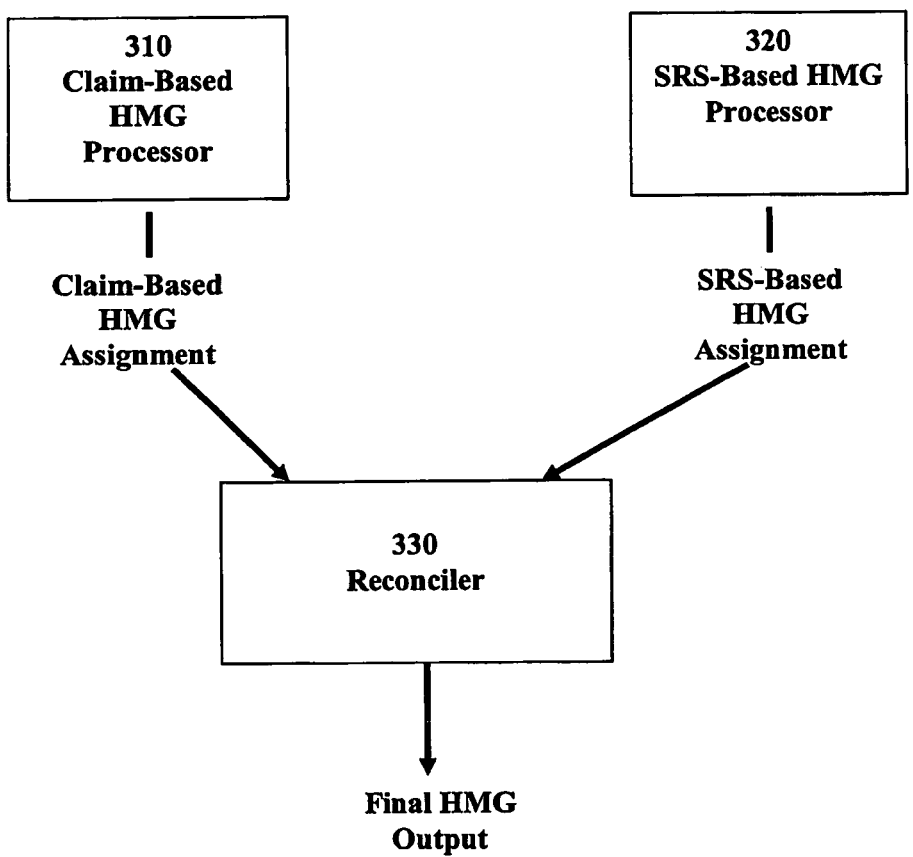
FIG. 3 provides an exemplary configuration of a health management group processor for use in system 100 in FIG. 1.

With reference to FIGS. 2 and 3, HMG processor 120 may perform at least the following functions: (210) assignment of one or more claim-based HMGs using medical, pharmacy and laboratory claim data available for each patient, wherein the processor 120 assigns a claim-based HMG to patients having associated claim data that meets the definition of the specific claim-based HMG; (220) assignment of one or more SRS-based HMGs using SRS data available for each patient, wherein the processor 120 assigns a SRS-based HMG to patients having associated SRS data that meets the definition of the specific SRS-based HMG; and (230) for each patient, reconciliation of the SRS-based and claim-based HMG assignments relating to the same disease, condition or pre-condition to provide a final HMG assignment for each disease, condition or pre-condition. The final HMG assignment is output (240), for example, in an output file.

As illustrated in FIG. 3, HMG processor 120 may contain modules 310, 320 and 330 that respectively perform functions 210, 220, and 230 described below and shown in FIG. 2.

Function 210 is performed by running a software program that analyzes each patient's claim data to determine whether the patient's claim data meets the predefined criteria of one or more predefined claim-based HMGs. In one implementation, the program assesses the diagnosis and procedure codes included in the patient's claim data, including ICD-9, DCC, NDC, CPT and HCPC codes, all of which may be provided in the medical, pharmaceutical and laboratory claims submitted to health insurance companies. Based upon the presence or absence of certain codes in a patient's claim data, processor 120 assigns the patient to one or more claim-based HMGs. The claim-based HMG assignments may represent both a specific disease, condition, or pre-condition and a level of severity or risk associated with the patient's disease, condition, or precondition (as described in the examples provided below). In one implementation, ETGs (discussed above) assigned to the patient claim data prior to input into the system 100 may also be identified and used to determine the appropriate HMG assignment by HMG processor 120.

Function 220, which may be performed in parallel or in series with function 210, is performed by running a software program that analyzes each patient's SRS data to determine whether the patient's claim data meets the predefined criteria of one or more predefined SRS-based HMGs. In one implementation, the program assesses preformatted SRS values associated with each patient to determine whether the SRS data meets the requirements of one or more predefined SRS-based HMGs. As with the claim-based HMG assignments, the SRS-based HMG assignments may represent both a specific disease, condition, or pre-condition, and a level of severity or risk associated with the patient's disease, condition, or pre-condition (as described in the examples provided below).

Once HMG processor 120 has assigned claim-based and SRS-based HMGs relating to a certain disease, condition, or pre-condition for each patient, processor 120 reconciles the claim-based HMG and the SRS-based HMG to obtain a final HMG for the patient relating to the particular disease, condition or pre-condition. Reconciliation of the claim-based and SRS-based HMGs may be performed based upon reconciliation definitions, for example, stored for each HMG in storage 110. The reconciliation definitions enable processor 120 to determine the level of severity of the disease, condition, or pre-condition that applies to the patient. This level of severity determines the final HMG for the particular disease, condition or pre-condition to be assigned to the patient. Examples of reconciliation definitions are provided below.

EXAMPLE 1

Assignment of HMGS for Sleep Disorders

I. Data Inputs:
Medical, laboratory and pharmacy claim data for previous 2 years (required)
Demographic data—sex, age, gender of patients (required) (used to facilitate the definitions of the HMGs and HMG severity levels)
SRS data on amount and intensity of sleep problems (desired, but not required)

II. Analysis of Claim Data for Sleep Problems (Function 210 in FIG. 2):

The patient's medical claim data is processed to identify whether one or more of the following codes appear in the patient's claim data:

- 95805 Multiple sleep latency or maintenance of wakefulness testing, recording, analysis and interpretation of physiological measurements of sleep during multiple trials to assess sleepiness
- 95806 Sleep study, simultaneous recording of ventilation, respiratory effort, ECG or heart rate, and oxygen saturation, unattended by a technologist
- 95807 Sleep study, simultaneous recording of ventilation, respiratory effort, ECG or heart rate, and oxygen saturation, attended by a technologist
- 95808 Polysomnography; sleep staging with 1-3 additional parameters of sleep, attended by a technologist
- 95810 Polysomnography; sleep staging with 4 or more additional parameters of sleep, attended by a technologist
- 95811 Polysomnography; sleep staging with 4 or more additional parameters of sleep, with initiation of continuous positive airway pressure therapy or bilevel ventilation, attended by a technologist
- 89.18 Other sleep disorder function tests
- 89.17 Polysomnogram
- 0016T-0187T Category III Codes
- 0088T Submucosal radiofrequency tissue volume reduction of tongue base, one or more sites, per session (ie, for treatment of obstructive sleep apnea syndrome)
- 0089T Actigraphy testing, recording, analysis and interpretation (minimum of three-day recording)

Additionally, the patient's pharmacy claim data is processed to identify the presence of any of the following DCC codes (shown with their associated drug):

| \multicolumn{4}{c}{PCCS 326-329 (SEDATIVE HYPNOTICS); PCC 330/331 (MISCELLANEOUS SLEEP-AIDS)} |
|---|---|---|---|
| pcc | Dcc | genericName | Information |
| 326 | 32603 | Amobarbital sodium | This drug is mainly used for insomnia. Could be used for pre-op sedation. |
| 326 | 32604 | Aprobarbital | Used as a sedative & as a hypnotic. Only with prescription directions would you be able to know the difference (dosed multiple times means sedative use; dosed at bedtime means hypnotic |
| 326 | 32605 | Butabarbital sodium | Used as a sedative & as a hypnotic. Only with prescription directions would you be able to know the difference (dosed multiple times means sedative use; dosed at bedtime means hypnotic |
| 326 | 32606 | Secobarbital sodium | This drug is mainly used for insomnia. Could be used for pre-op sedation. |
| 327 | 32700 | Amobarbital & secobarbital | Indication for sleep |
| 328 | 32800 | Estazolam | Indication for sleep |
| 328 | 32801 | Quazepam | Indication for sleep |
| 328 | 32802 | Temazepam | Indication for sleep but there is off-label use as an anti-anxiety agent. This off-label use is not approved because of drug dependency |
| 328 | 32803 | Triazolam | Indication for sleep |
| 328 | 32804 | Flurazepam hydrochloride | Indication for sleep |
| 329 | 32901 | Chloral hydrate | Used as a sedative & as a hypnotic. Also as a pre-op med. Only with prescription directions would you be able to know the difference (dosed multiple times means sedative use; dosed at bedtime means hypnotic. |
| 329 | 32902 | Ethchlorvynol | Indication for sleep |
| 329 | 32903 | Ethinamate | Indication for sleep |

-continued

| PCCS 326-329 (SEDATIVE HYPNOTICS); PCC 330/331 (MISCELLANEOUS SLEEP-AIDS) | | | |
|---|---|---|---|
| pcc | Dcc | genericName | Information |
| 329 | 32904 | Glutethimide | Indication for sleep |
| 329 | 32905 | Methyprylon | Indication for sleep-may be off the market now |
| 329 | 32908 | Zolpidem tartrate | Indication for sleep |
| 329 | 32909 | Zaleplon | Indication for sleep |
| 329 | 32911 | Eszopiclone | Indication for sleep |
| 329 | 32912 | Ramelteon | Indication for sleep |
| 330 | 33001 | Valerian extract, & in combination products | Herbal used for sleep |

Based upon the presence of one or more of the examinations, test, and/or drugs listed above, module 310 of HMG processor 120 assigns an HMG ("slp") and a severity level (0 (no problem) to 3 (most severe)) using the following process:

(1) First, the patient's medical and pharmacy claims are searched.

(2) If the patient's claim contains three or more of the following diagnosis and/or procedure codes within a given year and/or pharmacy claims indicating greater than or equal to three months of use of one or more of the following drugs during a given year, "slp03" (Sleep problems, most severe level) is assigned.

(3) If the patient's claim data contains only two of the diagnosis and/or procedure codes listed below and/or pharmacy claims indicating greater than or equal to two months of use of one or more of the following drugs during a given year, "slp02" (Sleep problems, moderate severity level) is assigned.

(4) If the patient's claim data contains only one of the diagnosis and/or procedure codes listed below and/or pharmacy claims indicating greater than or equal to one month of use of one or more of the following drugs during a given year, the "slp01" (Sleep problems, low severity level) assignment is maintained.

(5) If the patient's claim data does not include any of the diagnosis and/or procedure codes listed below and does not include any pharmacy claims indicating use of one or more of the drugs listed below during a given year, the "slp00" (No sleep problems) is assigned.

(6) If the patient's claim data is incomplete or missing and it cannot be determined whether the patient has a sleep problem, "slp00" is assigned.

| **Medical Codes: | | | | | |
|---|---|---|---|---|---|
| ICD9, CPT, HCPC or DCC | ICD9 | Procedure | DCC | ICD9_type | Time |
| 306.1 | X | | | sleep apnea (psychogenic) | within last 12 months |
| 307.4 | X | | | sleep disturbance (non-organic origin) | within last 12 months |
| 307.41 | X | | | sleeplessness; non organic origin | within last 12 months |
| 307.42 | X | | | Insomnia (primary) | within last 12 months |
| 307.45 | X | | | sleep disorder_non_organic_origin | within last 12 months |
| 307.49 | X | | | sleep disorder non-spec type NEC, subjective complaint | within last 12 months |
| 327.1 | X | | | Organic disorders of excessive somnolence [Organic hypersomnia] | within last 12 months |
| 327.2 | X | | | Organic sleep apnea | within last 12 months |
| 327.3 | X | | | Circadian rhythm sleep disorder | within last 12 months |
| 327.3 | X | | | Organic disorders of initiating and maintaining sleep [Organic insomnia] | within last 12 months |
| 327.4 | x | | | Organic parasomnia | within last 12 months |
| 327.5 | x | | | Organic sleep related movement disorders | within last 12 months |
| 327.8 | x | | | Other organic sleep disorders | within last 12 months |
| 626.2 | x | | | sleeplessness menopausal | within last 12 months |
| 770.4 | x | | | sleep disturbance NEC | within last 12 months |
| 770.81 | x | | | sleep apnea (essential) | within last 12 months |
| 770.81 | x | | | sleep apnea (primary) | within last 12 months |
| 770.82 | x | | | sleep apnea (obstructive) | within last 12 months |
| 770.82 | x | | | sleep apnea (specified NEC) | within last 12 months |
| 780.5 | x | | | sleep disturbance | within last 12 months |
| 780.51 | x | | | Insomnia + sleep apnea | within last 12 months |
| 780.52 | x | | | insomnia | within last 12 months |
| 780.53 | x | | | hypersomnia | within last 12 months |
| 780.55 | x | | | rhythm inversion | within last 12 months |
| 780.57 | x | | | sleep NEC | within last 12 months |
| 786.03 | x | | | sleep anea (spells) | within last 12 months |
| 307.4X | x | | | sleep disorder_non_organic_origin | within last 12 months |
| 327.X | x | | | organic sleep disorders | within last 12 months |
| 347.xx | x | | | paroxysmal | within last 12 months |
| 347.xx | x | | | Cataplexy + Narcolepsy | within last 12 months |
| 780.5X | x | | | sleep disorder_apnea | within last 12 months |
| 95805 | | x | | sleep latency test | within last 12 months |
| 95806 | | x | | sleep study | within last 12 months |
| 95807 | | x | | sleep study | within last 12 months |
| 95808 | | x | | polysomnography | within last 12 months |
| 95810 | | x | | polysomnography | within last 12 months |
| 95811 | | x | | polysomnography | within last 12 months |

-continued

| Medical Codes: | | | | | |
|---|---|---|---|---|---|
| ICD9, CPT, HCPC or DCC | ICD9 | Pro-cedure | DCC | ICD9_type | Time |
| 89.18 | | x | | evaluation - sleep disorder test | within last 12 months |
| 89.17 | | x | | polysomnogram | within last 12 months |
| 0088T | | x | | treat sleep apnea | within last 12 months |
| 0089T | | x | | actigraphy for sleep (3 day monitoring) | within last 12 months |
| See sleep meds list below | | | X | See sleep meds list below | within last 12 months |

Pharmacy Codes:
PCCS 326-329 (SEDATIVE HYPNOTICS); PCC 330/331 (MISCELLANEOUS SLEEP-AIDS)

| pcc | dcc | genericName | Information |
|---|---|---|---|
| 326 | 32603 | Amobarbital sodium | This drug is mainly used for insomnia. Could be used for pre-op sedation. |
| 326 | 32604 | Aprobarbital | Used as a sedative & as a hypnotic. Only with prescription directions would you be able to know the difference (dosed multiple times means sedative use; dosed at bedtime means hypnotic |
| 326 | 32605 | Butabarbital sodium | Used as a sedative & as a hypnotic. Only with prescription directions would you be able to know the difference (dosed multiple times means sedative use; dosed at bedtime means hypnotic |
| 326 | 32606 | Secobarbital sodium | This drug is mainly used for insomnia. Could be used for pre-op sedation. |

Pharmacy Codes:
PCCS 326-329 (SEDATIVE HYPNOTICS); PCC 330/331 (MISCELLANEOUS SLEEP-AIDS)

| pcc | dcc | genericName | Information |
|---|---|---|---|
| 327 | 32700 | Amobarbital & secobarbital | Indication for sleep |
| 328 | 32800 | Estazolam | Indication for sleep |
| 328 | 32801 | Quazepam | Indication for sleep |
| 328 | 32802 | Temazepam | Indication for sleep but there is off-label use as an anti-anxiety agent. This off-label use is not approved because of drug dependency |
| 328 | 32803 | Triazolam | Indication for sleep |
| 328 | 32804 | Flurazepam hydrochloride | Indication for sleep |
| 329 | 32901 | Chloral hydrate | Used as a sedative & as a hypnotic. Also as a pre-op med. Only with prescription directions would you be able to know the difference (dosed multiple times means sedative use; dosed at bedtime means hypnotic. |
| 329 | 32902 | Ethchlorvynol | Indication for sleep |
| 329 | 32903 | Ethinamate | Indication for sleep |
| 329 | 32904 | Glutethimide | Indication for sleep |
| 329 | 32905 | Methyprylon | Indication for sleep-may be off the market now |
| 329 | 32908 | Zolpidem tartrate | Indication for sleep |
| 329 | 32909 | Zaleplon | Indication for sleep |
| 329 | 32911 | Eszopiclone | Indication for sleep |
| 329 | 32912 | Ramelteon | Indication for sleep |
| 330 | 33001 | Valerian extract, & in combination products | Herbal used for sleep |

III. Analysis of SRS Data for Sleep Problems (Function 220 in FIG. 2):

The following flow chart illustrates an exemplary method of using SRS data (in the form of standardized patient responses to survey questions) to assign an SRS-based sleep problem HMG to each patient. In this flow chart, the "severe" level corresponds to "slp03" of the claim-based HMGs discussed above, while "moderate" corresponds to "slp02", "mild" corresponds to "slp01", and "nil" corresponds to "slp00."

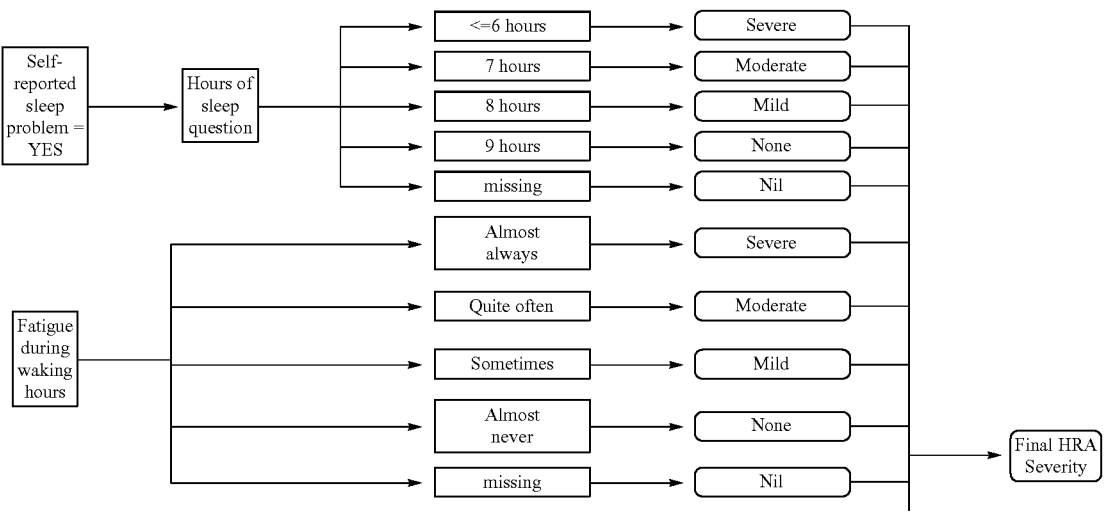

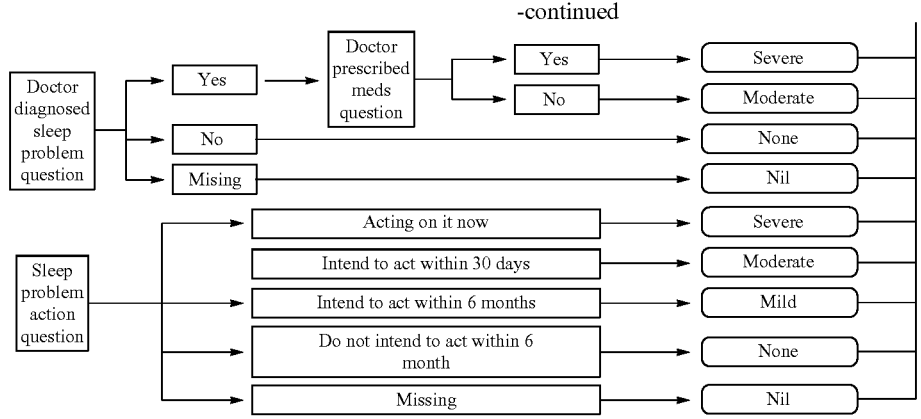

IV. Reconciling Claims-Based HMG and SRS-Based HMG Assignment (Function 230 in FIG. 2)

To determine the final HMG assignment, the following procedure is implemented (Function 230 in FIG. 2):

(1) If only a claim-based HMG assignment exists (i.e., no SRS data is available), then the claim-based HMG assignment becomes the final HMG assignment for the patient.

(2) If only an SRS-based HMG assignment exists (i.e., no claim data is available), then the SRS-based HMG assignment becomes the final HMG assignment for the patient.

(3) If both a claim-based HMG and SRS-based HMG assignments exist, the following chart is utilized to determine the final HMG assignment.

|  | Claims | | | | |
| --- | --- | --- | --- | --- | --- |
| SRS | Severe | Moderate | Low | None |
| Severe | Severe | Moderate | Moderate | Severe |
| Moderate | Severe | Moderate | Low | Moderate |
| Low | Moderate | Moderate | Low | Low |
| None | Severe | Moderate | Low | None |

The following chart provides an exemplary listing of how claim-based HMG and SRS-based HMG assignments may be reconciled into a final HMG assignment by module 330 of HMG processor 120:

| Final HMG Assignment | Claims_HMG | Claims HMG description | SRS_HMG | SRS HMG description |
| --- | --- | --- | --- | --- |
| Sleep03 | slp03 | severe sleep problems | Sleep5hours | Severe |
| Sleep03 | slp03 | severe sleep problems | Sleep6hours | Severe |
| Sleep03 | slp03 | severe sleep problems | FatigueSevere | Severe |
| Sleep03 | slp03 | severe sleep problems | NeedSleepSevere | Severe |
| Sleep03 | slp03 | severe sleep problems | NeedSleepSevere | Severe |
| Sleep03 | slp03 | severe sleep problems | SleepDisorderMedCare | Severe |
| Sleep03 | slp03 | severe sleep problems | TroubleSleepSevere | Severe |
| Sleep03 | slp03 | severe sleep problems | Sleep8hours | Mild |
| Sleep03 | slp03 | severe sleep problems | FatigueMild | Mild |
| Sleep03 | slp03 | severe sleep problems | NeedSleepMild | Mild |
| Sleep03 | slp03 | severe sleep problems | SleepDisorderCurrent | Mild |
| Sleep03 | slp03 | severe sleep problems | TroubleSleepMild | Mild |
| Sleep03 | slp03 | severe sleep problems | Sleep7hours | Moderate |
| Sleep03 | slp03 | severe sleep problems | FatigueModerate | Moderate |
| Sleep03 | slp03 | severe sleep problems | NeedSleepModerate | Moderate |
| Sleep03 | slp03 | severe sleep problems | SleepDiagnosisYes | Moderate |
| Sleep03 | slp03 | severe sleep problems | SleepMedsPresYes | Moderate |
| Sleep03 | slp03 | severe sleep problems | SleepMedsNonPresYes | Moderate |
| Sleep03 | slp03 | severe sleep problems | SleepDisorderMeds | Moderate |
| Sleep03 | slp03 | severe sleep problems | TroubleSleepModerate | Moderate |
| Sleep03 | slp03 | severe sleep problems | Sleep9hours | None |
| Sleep03 | slp03 | severe sleep problems | Sleep9hours | None |
| Sleep03 | slp03 | severe sleep problems | FatigueNone | None |
| Sleep03 | slp03 | severe sleep problems | NeedSleepNone | None |
| Sleep03 | slp03 | severe sleep problems | SleepDiagnosisNo | None |
| Sleep03 | slp03 | severe sleep problems | SleepMedsPresNo | None |
| Sleep03 | slp03 | severe sleep problems | SleepDisorderNever | None |
| Sleep03 | slp03 | severe sleep problems | SleepDisorderPast | None |
| Sleep03 | slp03 | severe sleep problems | TroubleSleepNone | None |
| Sleep02 | slp02 | moderate sleep problems | Sleep5hours | Severe |
| Sleep02 | slp02 | moderate sleep problems | Sleep6hours | Severe |
| Sleep02 | slp02 | moderate sleep problems | FatigueSevere | Severe |
| Sleep02 | slp02 | moderate sleep problems | NeedSleepSevere | Severe |
| Sleep02 | slp02 | moderate sleep problems | NeedSleepSevere | Severe |

-continued

| Final HMG Assignment | Claims_HMG | Claims HMG description | SRS_HMG | SRS HMG description |
|---|---|---|---|---|
| Sleep02 | slp02 | moderate sleep problems | SleepDisorderMedCare | Severe |
| Sleep02 | slp02 | moderate sleep problems | TroubleSleepSevere | Severe |
| Sleep02 | slp02 | moderate sleep problems | Sleep8hours | Mild |
| Sleep02 | slp02 | moderate sleep problems | FatigueMild | Mild |
| Sleep02 | slp02 | moderate sleep problems | NeedSleepMild | Mild |
| Sleep02 | slp02 | moderate sleep problems | SleepDisorderCurrent | Mild |
| Sleep02 | slp02 | moderate sleep problems | TroubleSleepMild | Mild |
| Sleep02 | slp02 | moderate sleep problems | Sleep7hours | Moderate |
| Sleep02 | slp02 | moderate sleep problems | FatigueModerate | Moderate |
| Sleep02 | slp02 | moderate sleep problems | NeedSleepModerate | Moderate |
| Sleep02 | slp02 | moderate sleep problems | SleepDiagnosisYes | Moderate |
| Sleep02 | slp02 | moderate sleep problems | SleepMedsPresYes | Moderate |
| Sleep02 | slp02 | moderate sleep problems | SleepMedsNonPresYes | Moderate |
| Sleep02 | slp02 | moderate sleep problems | SleepDisorderMeds | Moderate |
| Sleep02 | slp02 | moderate sleep problems | TroubleSleepModerate | Moderate |
| Sleep02 | slp02 | moderate sleep problems | Sleep9hours | None |
| Sleep02 | slp02 | moderate sleep problems | Sleep9hours | None |
| Sleep02 | slp02 | moderate sleep problems | FatigueNone | None |
| Sleep02 | slp02 | moderate sleep problems | NeedSleepNone | None |
| Sleep02 | slp02 | moderate sleep problems | SleepDiagnosisNo | None |
| Sleep02 | slp02 | moderate sleep problems | SleepMedsPresNo | None |
| Sleep02 | slp02 | moderate sleep problems | SleepDisorderNever | None |
| Sleep02 | slp02 | moderate sleep problems | SleepDisorderPast | None |
| Sleep02 | slp02 | moderate sleep problems | TroubleSleepNone | None |
| Sleep02 | slp01 | mild sleep problems | Sleep5hours | Severe |
| Sleep02 | slp01 | mild sleep problems | Sleep6hours | Severe |
| Sleep02 | slp01 | mild sleep problems | FatigueSevere | Severe |
| Sleep02 | slp01 | mild sleep problems | NeedSleepSevere | Severe |
| Sleep02 | slp01 | mild sleep problems | NeedSleepSevere | Severe |
| Sleep02 | slp01 | mild sleep problems | SleepDisorderMedCare | Severe |
| Sleep02 | slp01 | mild sleep problems | TroubleSleepSevere | Severe |
| Sleep01 | slp01 | mild sleep problems | Sleep8hours | Mild |
| Sleep01 | slp01 | mild sleep problems | FatigueMild | Mild |
| Sleep01 | slp01 | mild sleep problems | NeedSleepMild | Mild |
| Sleep01 | slp01 | mild sleep problems | SleepDisorderCurrent | Mild |
| Sleep01 | slp01 | mild sleep problems | TroubleSleepMild | Mild |
| Sleep01 | slp01 | mild sleep problems | Sleep7hours | Moderate |
| Sleep01 | slp01 | mild sleep problems | FatigueModerate | Moderate |
| Sleep01 | slp01 | mild sleep problems | NeedSleepModerate | Moderate |
| Sleep01 | slp01 | mild sleep problems | SleepDiagnosisYes | Moderate |
| Sleep01 | slp01 | mild sleep problems | SleepMedsPresYes | Moderate |
| Sleep01 | slp01 | mild sleep problems | SleepMedsNonPresYes | Moderate |
| Sleep01 | slp01 | mild sleep problems | SleepDisorderMeds | Moderate |
| Sleep01 | slp01 | mild sleep problems | TroubleSleepModerate | Moderate |
| Sleep01 | slp01 | mild sleep problems | Sleep9hours | None |
| Sleep01 | slp01 | mild sleep problems | Sleep9hours | None |
| Sleep01 | slp01 | mild sleep problems | FatigueNone | None |
| Sleep01 | slp01 | mild sleep problems | NeedSleepNone | None |
| Sleep01 | slp01 | mild sleep problems | SleepDiagnosisNo | None |
| Sleep01 | slp01 | mild sleep problems | SleepMedsPresNo | None |
| Sleep01 | slp01 | mild sleep problems | SleepDisorderNever | None |
| Sleep01 | slp01 | mild sleep problems | SleepDisorderPast | None |
| Sleep01 | slp01 | mild sleep problems | TroubleSleepNone | None |
| Sleep00 | slp00 | no sleep problems | Sleep9hours | None |
| Sleep00 | slp00 | no sleep problems | Sleep9hours | None |
| Sleep00 | slp00 | no sleep problems | FatigueNone | None |
| Sleep00 | slp00 | no sleep problems | NeedSleepNone | None |
| Sleep00 | slp00 | no sleep problems | SleepDiagnosisNo | None |
| Sleep00 | slp00 | no sleep problems | SleepMedsPresNo | None |
| Sleep00 | slp00 | no sleep problems | SleepDisorderNever | None |
| Sleep00 | slp00 | no sleep problems | SleepDisorderPast | None |
| Sleep00 | slp00 | no sleep problems | TroubleSleepNone | None |

Figure 4:
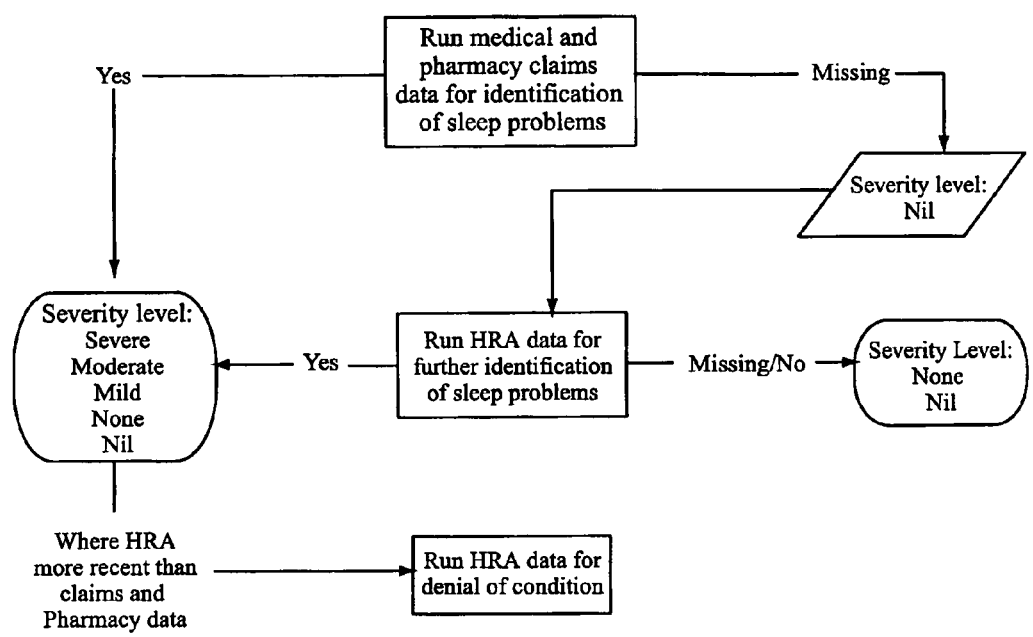
FIG. 4 provides an exemplary flow chart of a processing method performed by the health management group processor of FIGS. 1 and 3.

An exemplary flow chart of function 230 performed by module 330 of HMG processor 120 for assignment of HMGs relating to sleeping disorders or problems is provided in FIG. 4. As shown in FIG. 4, the HMG processor 120 analyzes patient claim data to identify sleep-related examinations, treatments, tests or other problems as described above. If no problems are identified in the patient claim data and health risk assessment (HRA) data, which is analogous to SRS data in this example, is available for the patient(s), the HRA data is analyzed as described above. If no sleep problems are identified in either the patient's claim or HRA data, the patient is assigned a severity level of "0."

If the patient's claim data or HRA data indicates that the patient has sleep problems, the patient is assigned to an HMG severity level as defined above. In the case of claim-based HMG assignment, if the HRA data available for the patient is more recent than the claim/pharmacy data for the patient, an HRA-based HMG assessment may also be run to determine whether the claim-based HMG assignment is still valid (403).

EXAMPLE 2

Assignment of HMGS for Alcohol Problems

I. Data Inputs:

Medical and pharmacy claim data for at least the previous one year (required)

Demographic data—sex, age, gender of patients (required) (used to facilitate the definitions of the HMGs and HMG severity levels)

SRS data collected within past one year (required)

II. Analysis of Claim Data for Alcohol Problems (Function 210 in FIG. 2):

Alcohol-problem HMGs may be assigned to a patient based upon the presence of one or more alcohol-related health problems in the patient's medical and/or pharmacy claim data. For example, the presence of one or more of the following treatments or conditions (listed by ICD-9, CPT and HCPC codes) in a patient's claim data (within the past year) enables HMG processor 120 to assign a claim-based HMG with an associated stage for the patient (function 210 in FIG. 2):

---

- 291 Alcohol-induced mental disorders
  - 291.8 Other specified alcohol-induced mental disorders
  - 291.9 Unspecified alcohol-induced mental disorders
  - 291.4 Idiosyncratic alcohol intoxication
  - 291.1 Alcohol-induced persisting amnestic disorder
  - 291.5 Alcohol-induced psychotic disorder with delusions
  - 291.0 Alcohol withdrawal delirium
  - 291.3 Alcohol-induced psychotic disorder with hallucinations
  - 291.2 Alcohol-induced persisting dementia
- H0001-H2037 Alcohol and Drug Abuse Treatment Services H0001-H2037
  - H0029 Alcohol and/or drug prevention alternatives service (services for populations that exclude alcohol and other drug use e.g., alcohol free social events)
  - H0047 Alcohol and/or other drug abuse services, not otherwise specified
  - H0049 Alcohol and/or drug screening
  - H0050 Alcohol and/or drug services, brief intervention, per 15 minutes
  - H0001 Alcohol and/or drug assessment
  - H0006 Alcohol and/or drug services; case management
  - H0021 Alcohol and/or drug training service (for staff and personnel not employed by providers)
  - H0022 Alcohol and/or drug intervention service (planned facilitation)
  - H2035 Alcohol and/or other drug treatment program, per hour
  - H2036 Alcohol and/or other drug treatment program, per diem
  - H0003 Alcohol and/or drug screening; laboratory analysis of specimens for presence of alcohol and/or drugs
  - H0005 Alcohol and/or drug services; group counseling by a clinician
  - H0007 Alcohol and/or drug services; crisis intervention (outpatient)
  - H0008 Alcohol and/or drug services; subacute detoxification (hospital inpatient)
  - H0009 Alcohol and/or drug services; acute detoxification (hospital inpatient)
  - H0010 Alcohol and/or drug services; subacute detoxification (residential addiction program inpatient)
  - H0011 Alcohol and/or drug services; acute detoxification (residential addiction program inpatient)
  - H0012 Alcohol and/or drug services; subacute detoxification (residential addiction program outpatient)
  - H0013 Alcohol and/or drug services; acute detoxification (residential addiction program outpatient)
  - H0014 Alcohol and/or drug services; ambulatory detoxification
  - H0016 Alcohol and/or drug services; medical/somatic (medical intervention in ambulatory setting)
  - H0027 Alcohol and/or drug prevention environmental service (broad range of external activities geared toward modifying systems in order to mainstream prevention through policy and law)
  - H2034 Alcohol and/or drug abuse halfway house services, per diem
  - H0048 Alcohol and/or other drug testing: collection and handling only, specimens other than blood
  - H0015 Alcohol and/or drug services; intensive outpatient (treatment program that operates at least 3 hours/day and at least 3 days/week and is based on an individualized treatment plan), including assessment, counseling; crisis intervention, and activity therap
  - H0020 Alcohol and/or drug services; methadone administration and/or service (provision of the drug by a licensed program)
- 305.0 Nondependent alcohol abuse
- E860 Accidental poisoning by alcohol, not elsewhere classified
  - E860.0 Accidental poisoning by alcoholic beverages
  - E860.9 Accidental poisoning by unspecified alcohol
- T1000-T5999 National T Codes Established for State Medicaid Agencies T1000-T9999
  - T1007 Alcohol and/or substance abuse services, treatment plan development and/or modification
  - T1012 Alcohol and/or substance abuse services, skills development
  - T1006 Alcohol and/or substance abuse services, family/couple counseling
  - T1010 Meals for individuals receiving alcohol and/or substance abuse services (when meals not included in the program)
- 760 Fetus or newborn affected by maternal conditions which may be unrelated to present pregnancy (health of the mother and effects on a fetus)
- 82000-84999 Chemistry
  - 82075 Alcohol (ethanol); breath
- 99406-99409 Behavior Change Interventions, Individual
  - 99408 Alcohol and/or substance (other than tobacco) abuse structured screening (eg, AUDIT, DAST), and brief intervention (SBI) services; 15 to 30 minutes
  - 99409 Alcohol and/or substance (other than tobacco) abuse structured screening (eg, AUDIT, DAST), and brief intervention (SBI) services; greater than 30 minutes
- 790 Nonspecific findings on examination of blood
  - 790.3 Excessive blood level of alcohol
- 4000E-4250F Therapeutic, Preventive or Other Interventions
  - 4158F Patient education regarding risk of alcohol consumption performed (HEP-C)1
- G0008-G3001 Untitled section
  - G0396 Alcohol and/or substance (other than tobacco) abuse structured assessment (e.g., audit, dast), and brief intervention 15 to 30 minutes
  - G0397 Alcohol and/or substance (other than tobacco) abuse structured assessment (e.g., audit, dast), and intervention, greater than 30 minutes
- 303 Alcohol dependence syndrome
  - 303.9 Other and unspecified alcohol dependence
- 94 Procedures related to the psyche
  - 94.6 Alcohol and drug rehabilitation and detoxification
- 977 Poisoning by other and unspecified drugs and medicinal substances
  - 977.3 Poisoning by alcohol deterrents
- E947 Other and unspecified drugs and medicinal substances causing adverse effect in therapeutic use
  - E947.3 Alcohol deterrents causing adverse effect in therapeutic use
- V70 General medical examination
  - V70.4 Examination for medicolegal reason; including alcohol problems
- 980 Toxic effect of alcohol
  - 980.0 Toxic effect of ethyl alcohol
  - H0008 Alcohol and/or drug services; subacute detoxification (hospital inpatient)
  - H0009 Alcohol and/or drug services; acute detoxification (hospital inpatient)
  - H0010 Alcohol and/or drug services; subacute detoxification (residential addiction program inpatient)
  - H0011 Alcohol and/or drug services; acute detoxification (residential addiction program inpatient)
  - H0012 Alcohol and/or drug services; subacute detoxification (residential addiction program outpatient)

-continued

| | |
|---|---|
| ⬛ H0013 | Alcohol and/or drug services; acute detoxification (residential addiction program outpatient) |
| ⬛ H2034 | Alcohol and/or drug abuse halfway house services, per diem |

| DCC | Drug |
|---|---|
| DCC 83701 | Disulfiram |
| DCC 82102 | Naltrexone; only can be used with an alcohol claim, per Artz |
| DCC 83708 | Acamprosate |

Claim-based alcohol-problem HMGs having an associated stage (representing the level of severity of the alcohol-related problems) may be assigned as follows based upon the presence of one or more of the above-listed medical or pharmacy codes:

| HMG | Stage | Requirements |
|---|---|---|
| ALC | Stage 0 | No alcohol problems indicated through no medical or pharmacy claims related to alcohol problems |
| ALC | Stage 1 | Alcohol_Diag of (ICD9) for alcohol problems<br>Alc_RX: or DCC for alcoholism/drinking/craving (see list above)<br>Alc_Stays: plus NO procedure of service indicator for an inpatient, residential or halfway house stay within the last year due to alcohol<br>Alc_Proc: but a CPT or HCPC related to outpatient alcohol treatment |
| ALC | Stage 2 | Alc_Diag of (ICD9) information for alcohol problems,<br>Alc_Stays: plus NO procedure or service indicator for an inpatient, residential or halfway house stay within the last year due to alcohol<br>Alc_Proc: plus NO CPT or HCPC related to outpatient alcohol treatment<br>Alc_RX: plus NO (DCC for alcoholism/drinking/craving) (see list above) |
| ALC | Stage 3 | Alc_Diag: ICD9 information for alcohol problems<br>Alc_RX: or (DCC for alcoholism/drinking/craving) (see list above)<br>Alc_Stays: AND a procedure or service indicator for an inpatient, residential or halfway house stay within the last year<br>Alc_Proc: this level is not dependent on a CPT code |

III. Analysis of SRS Data for Alcohol Problems (Function 220 in FIG. 2):

SRS data, such as data collected from patient surveys, may be used to assign alcohol-related HMGs and associated severity levels to patients. For example, patients may provide answers to the following questions, and the answers may correspond to a defined level of severity (stages 0-3 in the example provided below):

| WebMD ™ Survey | | | |
|---|---|---|---|
| Dimensional Concept | Question | Answer | Level of Severity of Alcohol Problem |
| Quantity-daily | How much alcohol do you typically consume daily? | I don't drink alcohol | Stage 0 |
| | | Less than 1 | Stage 0 |
| | | 1-2 drinks | Stage 1 |
| | | Greater 2 drinks | Stage 2 |

| WebMD ™ Survey | | | |
|---|---|---|---|
| Dimensional Concept | Question | Answer | Level of Severity of Alcohol Problem |
| Cut-back | I have tried to cut back on my alcohol use | Check box | Stage 1 |
| Others_Alcohol_Perception | I sometimes get annoyed with others commenting on my drinking | Check box | Stage 1 |
| Alcohol_Guilt | I sometimes feel guilty about my drinking | Check box | Stage 1 |
| Quantity_Morning | I sometimes drink in the morning | Check box | Stage 1 |
| Stages of Change_Alcohol | Reduce alcohol | Not intending to take action | No level determination |
| | | Intending to take action 6 months | Stage 1 |
| | | Intending to take action 30 days | Stage 1 |
| | | Action on it now - no more than 6 months | Stage 1 |
| | | Acting on it now - more than 6 months | Stage 1 |
| Quantity-daily | How much alcohol do you typically consume daily? | I don't drink alcohol | Stage 0 |
| | | Less than or up to 1 drink | Stage 0 |
| | | 2 drinks | Stage 1 |
| | | Greater 2 drinks | Stage 2 |

Additional and/or different questions may also be utilized to assign a level of severity for each patient.

IV. Reconciling Claims-Based HMG and SRS-Based HMG Assignment (Function 230 in FIG. 2)

Once both a claims-based HMG group with associated severity level and an SRS-based group with an associated severity level has been assigned, the two HMG assignments may be reconciled using the following table:

| | Claims Severity Level | | | |
|---|---|---|---|---|
| SRS Severity | Stage 3 | Stage 2 | Stage 1 | No Alcohol Problems in Claims |
| Stage II | Stage 3 | Stage 2 | Stage 1 | Stage 2 |
| Stage I | Stage 3 | Stage 2 | Stage 1 | Stage 1 |
| No Alcohol Problems from SRS | Stage 3 | Stage 2 | Stage 1 | Stage 0 (No Alcohol Problems) |

The examples provided above are intended to be illustrative of the methodology of the present invention and are not intended to limit the application of the present invention. Many other types of HMGs are contemplated within the scope of the present invention, including HMGs defined for different diseases, acute and chronic health conditions, and pre-conditions (increased likelihood of developing a disease or health condition in the future). Additional mapping of various types of patient health data that may be provided as inputs to the system 100 (described above with reference to FIG. 1) may also be implemented to enable accurate HMG assignment by HMG processor 120.

The HMGs assigned using the methodology of the present invention described above may be stored, for example, as output files in storage 130 of FIG. 1. The HMGs assigned by HMG processor 120 may also be provided to an optional display generator, such as display component 140 in FIG. 1, which may generate a graphic display to enable users to identify the HMGs assigned to one or more patients, to identify patients for intervention, and/or for other desired purposes. Such a graphic display may be web-based to enable access to the HMGs via browser technology.

Exemplary web-based graphic displays of the HMG data generated by HMG processor 120 are provided in FIGS. 5-9. In these drawings, HMGs are synonymous with the HMGs described above.

FIG. 5 depicts an exemplary display in which "HMG" information is displayed to a user and links to the HMGs are also provided. In FIG. 5, a plurality of members of a health plan are listed by member identification number. HMGs relating to intervention opportunities ("Intvntn. Opps."), Smoking/Tobacco Use, Obesity and Exercise are displayed. For each member, a colored display box is provided under each HMG to illustrate the HMG severity level assigned to each member for each HMG. For example, a first color (such as green) may indicate that the member has been assigned to the lowest severity level for a given HMG (i.e., severity of 0 indicating that the member does not have any problem), a second color (such as yellow) may indicate that the member has been assigned to a low severity level for a given HMG (i.e., severity of 1 indicating that the member has a low severity), a third color (such as orange) may indicate that the member has been assigned to a moderate severity level for a given HMG (i.e., severity of 2 indicating that the member has moderate severity), and a fourth color (such as red) may indicate that the member has been assigned to the highest severity level (i.e., a severity of 3). In FIG. 5, the four severity levels are depicted in varying shades of grey, from light (severity level 0) to dark (severity level 3). Alternatively, other graphic display techniques may be implemented, such as numeric severity level displays, graphic symbols, etc., to enable a user to visually determine the HMG severity level assigned to each member for each displayed HMG.

Figure 6:
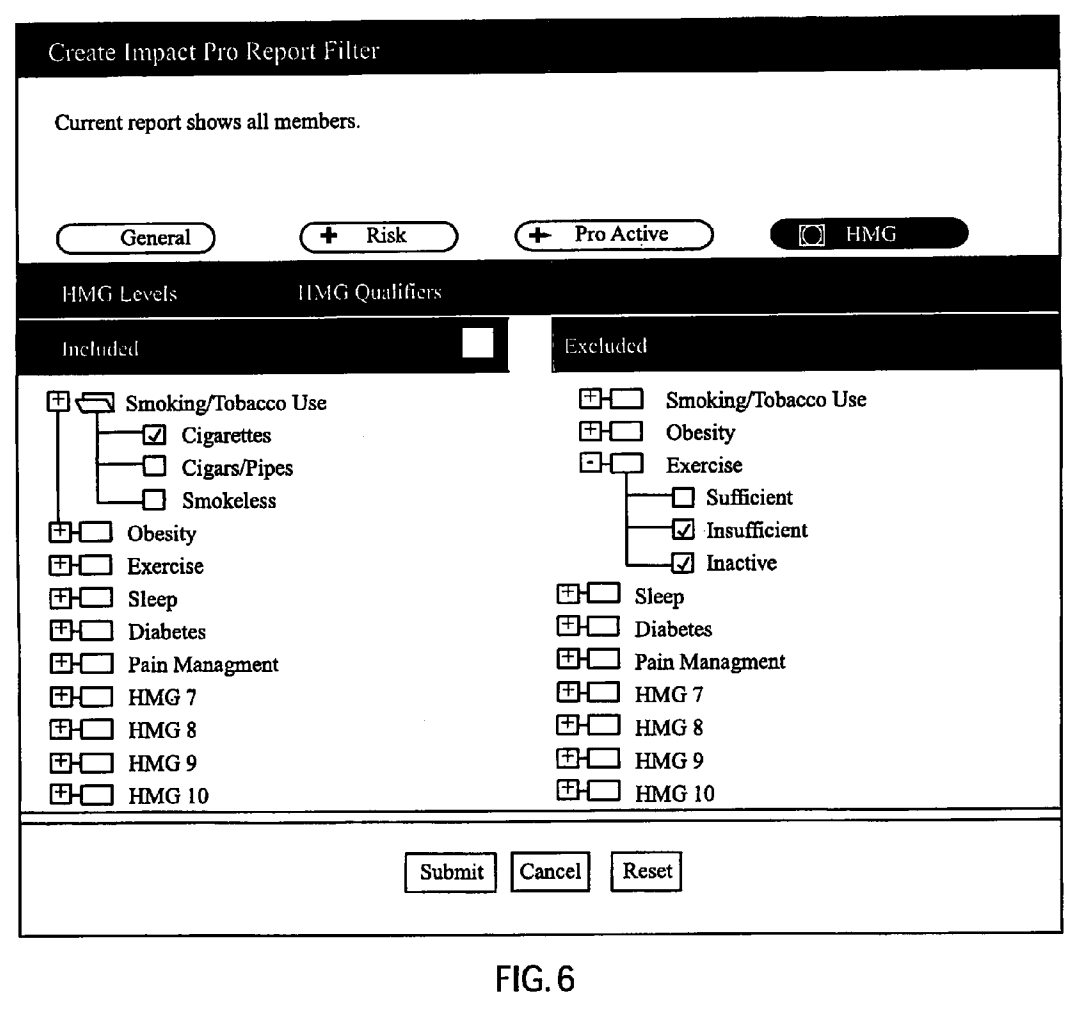

FIG. 6 depicts an exemplary graphic user interface that enables a user to enter filter criteria to enable the user to identify members having one or more conditions or assigned to one or more HMGs. By selecting desired filter criteria, the user may identify all members having the selected criteria.

Figure 7:
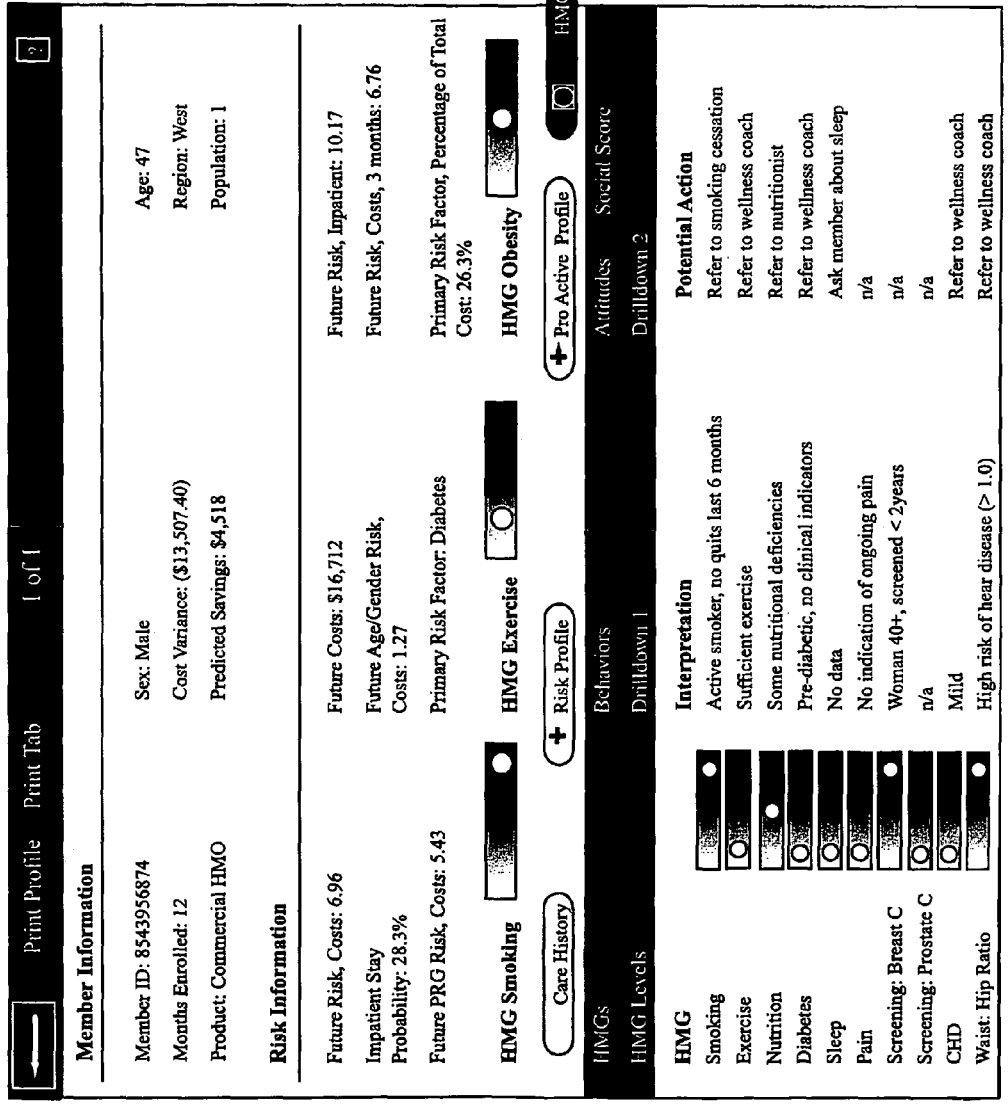

FIG. 7 depicts exemplary HMG data associated with a selected member, including a list of HMGs, a visual depiction of the member's level of severity for each HMG, an interpretation of the member's data relating to each HMG, and potential action that may be taken with the patient relating to each HMG.

Figure 8:
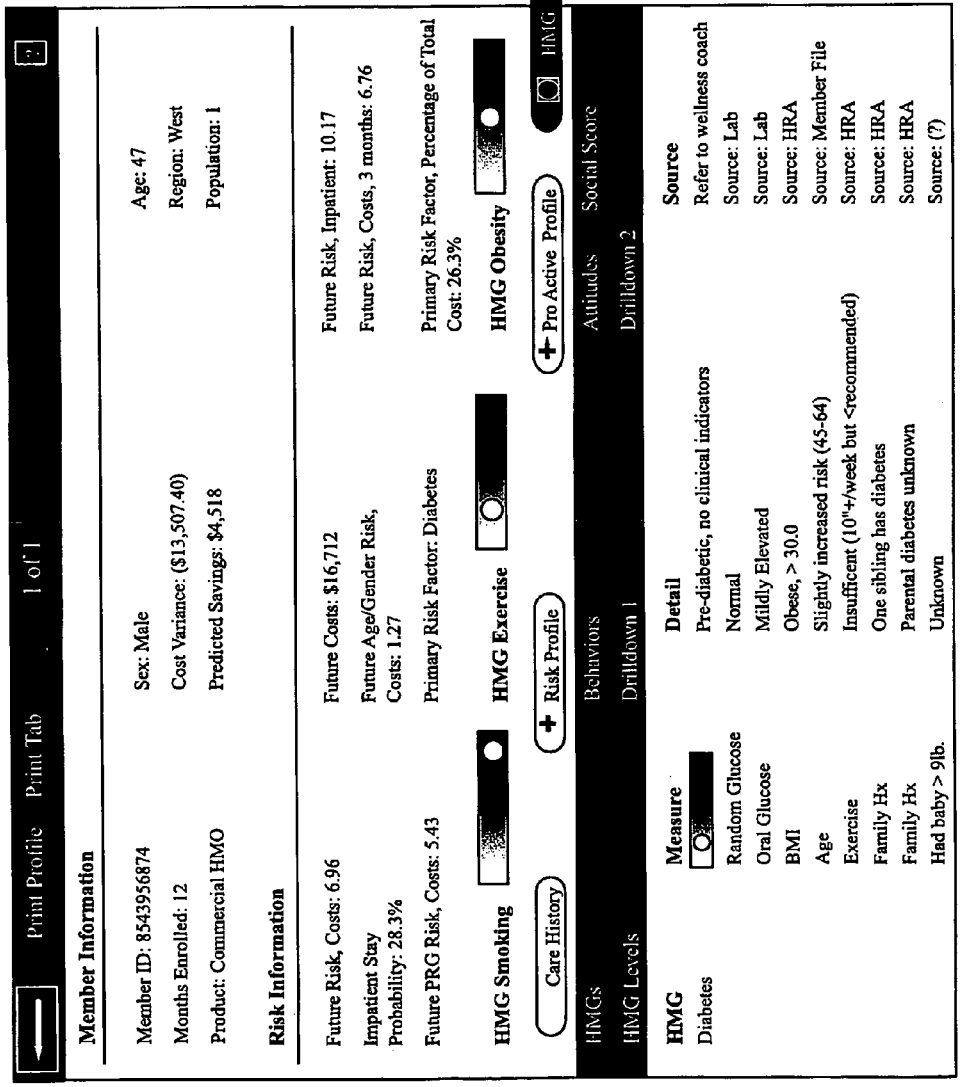

FIG. 8 provides an exemplary first drilldown level with respect to a selected HMG (diabetes is selected here) from the HMGs listed on the screen in FIG. 7. The displayed data indicates the tests or measures for the member taken from the member's claim and/or SRS data, as well as details concerning each measurement and the source of the data.

Figure 9:
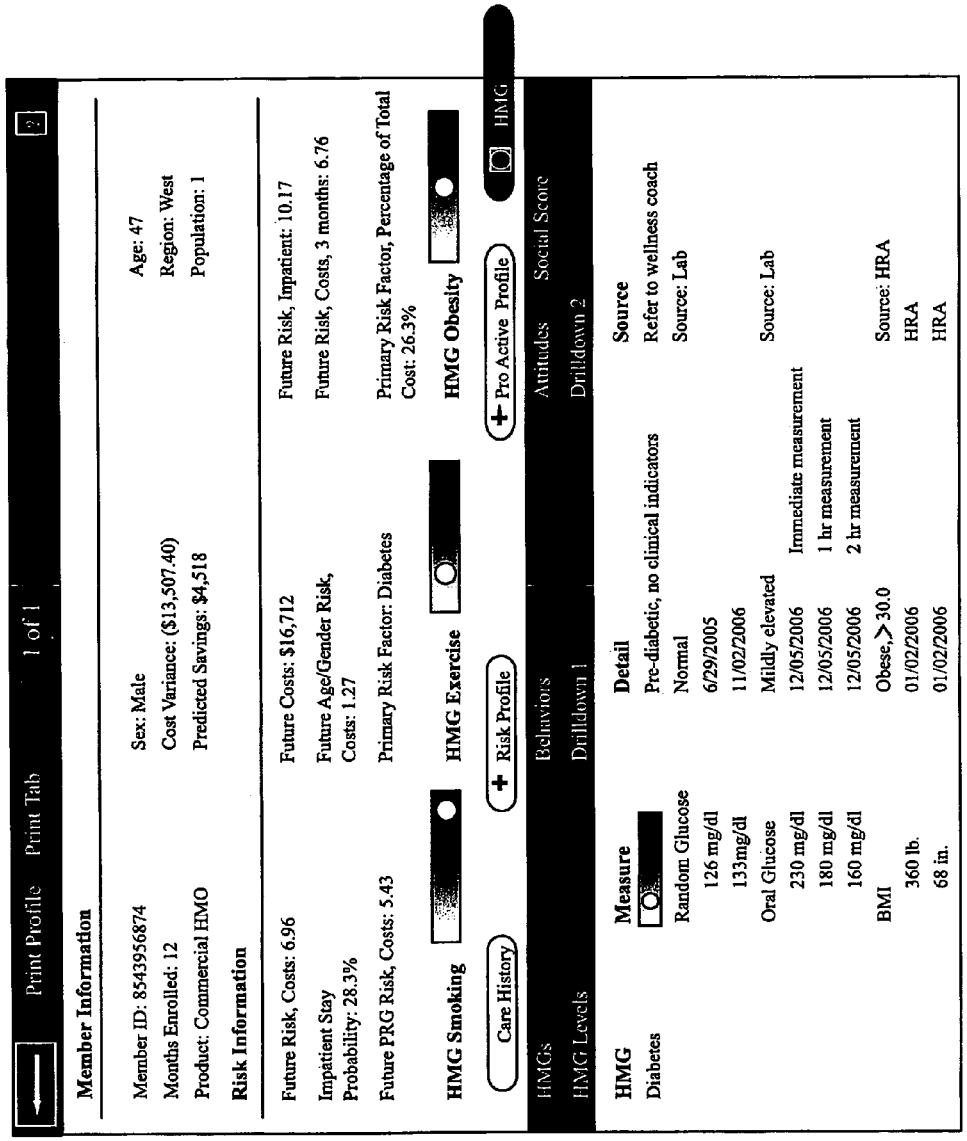

FIG. 9 depicts an exemplary second drilldown level with respect to the measurements associated with the member as displayed in FIG. 8. Further details of each measurement are displayed, including levels, dates of measurement, and the source of the data.

From the above description and drawings, it will be understood by those of ordinary skill in the art that the particular embodiments shown and described are for purposes of illustration only and are not intended to limit the scope of the present invention. Those of ordinary skill in the art will recognize that the present invention may be embodied in other specific forms without departing from its spirit or essential characteristics. References to details of particular embodiments are not intended to limit the scope of the invention.

What is claimed is:

1. A computer-implemented method for generating health management data for one or more patients relating to a disease, health condition or pre-condition, comprising a computer system performing the following:

storing, using a computer database, a plurality of health management groups, each relating to a disease, health condition or pre-condition and comprising one or more medical codes associated with the disease, health condition, or pre-condition, a health management group definition related to self-report survey data associated with the disease, health condition, or pre-condition, and an associated severity level;

storing mapping data that enables mapping of self-report survey data obtained from a patient to one or more of the stored health management groups based on health management group definitions related to self-report survey data using the computer database;

receiving, at a computer processor, medical claim data and self-report survey data associated with the patient, the received self-report survey data obtained from the patient and having no defined medical code;

determining whether the medical claim data for the patient contains one or more of the stored medical codes associated with the disease, health condition or pre-condition using the computer processor;

assigning the patient to a first health management group having a first associated severity level using at least the medical codes in the patient's medical claim data using the computer processor;

assigning the patient to a second health management group having a second severity level using the received self-report survey data and the stored mapping data using the computer processor;

reconciling the first and second health management groups using predefined reconciliation rules to generate a final health management group having an associated severity level for the patient for the disease, health condition or pre-condition using the computer processor; and storing the final health management group generated for the patient in the computer database.

2. The method of claim 1, further comprising:

generating display data that displays the final health management group for the patient.

3. A computer-implemented method for generating health management data for one or more patients relating to a plurality of diseases, health conditions and pre-conditions, comprising a computer system performing the following:

storing, using a computer database, a plurality of health management groups relating to a plurality of diseases, health conditions and pre-conditions, wherein each health management group relates to a disease, health condition or pre-condition and comprises one or more medical codes associated with the disease, health condition, or pre-condition, a health management group definition related to self-report survey data associated with the disease, health condition, or pre-condition, and an associated severity level;

storing mapping data that enables mapping of self-report survey data obtained from a patient to one or more of the stored health management groups based on health management group definitions related to self-report survey data using the computer database;

receiving, at a computer processor, medical claim data and self-report survey data associated with the patient, the received self-report survey data obtained from the patient and having no defined medical code;

determining whether the medical claim data for the patient contains one or more of the stored medical codes associated with one or more of the stored diseases, health condition and pre-conditions using the computer processor;

assigning the patient to a first health management group having a first associated severity level based upon the presence or absence of medical codes in the patient's medical claim data using the computer processor;

assigning the patient to a second health management group having a second severity level using the received self-report survey data and the stored mapping data using the computer processor;

determining the first and second health management groups relate to the same disease, health condition or pre-condition using the computer processor; and reconciling the first and second health management groups using predefined reconciliation rules to generate a final health management group having the first or the second severity level for the patient for the disease, health condition or pre-condition using the computer processor.

4. The method of claim 3, further comprising:
generating display data that displays the final health management group for the patient.

5. The method of claim 3, further comprising storing the final health management group generated for the patient using the computer database.

6. A computer-implemented system for generating health management data for one or more patients relating to a disease, health condition or pre-condition, comprising:
(a) a database storing:
    a plurality of health management groups, each relating to a disease, health condition or pre-condition and comprising:
        one or more medical codes associated with the disease, health condition, or pre-condition,
        a health management group definition related to self-report survey data associated with the disease, health condition, or pre-condition, and
        an associated severity level; and
    mapping data that enables mapping of self-report survey data obtained from a patient to one or more of the stored health management groups based on health management group definitions related to self-report survey data; and
(b) a processor configured to:
    receive medical claim data and self-report survey data associated with the patient, the received self-report survey data obtained from the patient and having no defined medical code;
    determine whether the medical claim data for the patient contains one or more of the stored medical codes associated with the disease, health condition or pre-condition;
    assign the patient to a first health management group having a first associated severity level using at least the medical codes in the patient's medical claim data;
    assign the patient to a second health management group having a second severity level using the received self-report survey data and the stored mapping data;
    reconcile the first and second health management groups using predefined reconciliation rules to generate a final health management group having an associated severity level for the patient for the disease, health condition or pre-condition.

7. The system of claim 6, further comprising:
a display for displaying the final health management group for the patient.

8. The system of claim 6, wherein the database further stores the final health management group generated for the patient.

9. A computer-implemented system for generating health management data for one or more patients relating to a disease, health condition or pre-condition, comprising:
(a) a database storing:
    a plurality of health management groups relating to a plurality of diseases, health conditions and pre-conditions, wherein each health management group relates to a disease, health condition or pre-condition and comprises:
        one or more medical codes associated with the disease, health condition, or pre-condition,
        a health management group definition related to self-report survey data associated with the disease, health condition, or pre-condition, and
        an associated severity level; and
    mapping data that enables mapping of self-report survey data obtained from a patient to one or more of the stored health management groups based on health management group definitions related to self-report survey data; and
(b) a processor configured to:
    receive medical claim data and self-report survey data associated with the patient, the received self-report survey data obtained from the patient and having no defined medical code;
    determine whether the medical claim data for the patient contains one or more of the stored medical codes associated with one or more of the stored diseases, health condition and pre-conditions;
    assign the patient to a first health management group having a first associated severity level based upon the presence or absence of medical codes in the patient's medical claim data;
    assign the patient to a second health management group having a second severity level using the received self-report survey data and the stored mapping data;
    determine the first and second health management groups relate to the same disease, health condition or pre-condition; and
    reconcile the first and second health management groups using predefined reconciliation rules to generate a final health management group having the first or the second severity level for the patient for the disease, health condition or pre-condition.

10. The system of claim 9, further comprising:
a display for displaying the final health management group for the patient.

11. The system of claim 9, wherein the database further stores the final health management group generated for the patient.

* * * * *

UNITED STATES PATENT AND TRADEMARK OFFICE
CERTIFICATE OF CORRECTION

PATENT NO.       : 8,775,200 B1
APPLICATION NO.  : 12/195858
DATED            : July 8, 2014
INVENTOR(S)      : Daniel L. Dunn and Michael Manocchia Page 1 of 1

It is certified that error appears in the above-identified patent and that said Letters Patent is hereby corrected as shown below:

Specification

| Column | Line | PTO | Should Be |
|---|---|---|---|
| 4 | 21 | "Medical claims," which is incorporated" | Medical Claims," which is incorporated |
| 7 | 60 | "Assignment of HMGS for Sleep Disorders" | Assignment of HMGs for Sleep Disorders |
| 13 | flowchart | " 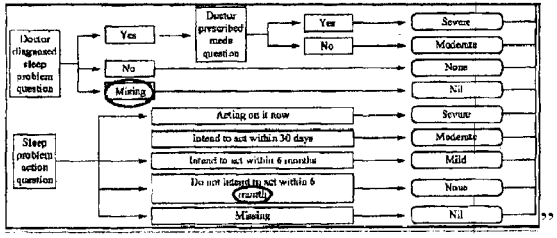 " | Should read respectively:<br>• missing<br>• months |
| 13 | 56 | "FatigueS evere" | FatigueSevere |
| 13 | 62 | "FatigueS evere" | FatigueSevere |
| 17 | 3 | "Assignment of HMGS for Alcohol Problems" | Assignment of HMGs for Alcohol Problems |
| 18 | 36 | "4000E-4250F" | 4000F-4250F |

Signed and Sealed this
Seventh Day of October, 2014

Michelle K. Lee
*Deputy Director of the United States Patent and Trademark Office*